(12) United States Patent
Hector

(10) Patent No.: US 9,506,097 B1
(45) Date of Patent: Nov. 29, 2016

(54) SYNTHETIC PROMOTER FOR XYLOSE-REGULATED GENE EXPRESSION

(71) Applicant: The United States of America, as represented by the Secretary of Agriculture, Washington, DC (US)

(72) Inventor: Ronald E. Hector, Washington, IL (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 14/796,125

(22) Filed: Jul. 10, 2015

(51) Int. Cl.
*C12P 19/02* (2006.01)
*C12N 15/81* (2006.01)
*C12P 19/14* (2006.01)

(52) U.S. Cl.
CPC ............... *C12P 19/02* (2013.01); *C12N 15/81* (2013.01); *C12P 19/14* (2013.01)

(58) Field of Classification Search
None
See application file for complete search history.

(56) References Cited

U.S. PATENT DOCUMENTS

| 5,650,294 A | 7/1997 | Kurth et al. |
| 8,802,412 B2 | 8/2014 | Teramoto et al. |

OTHER PUBLICATIONS

Steiner, Sabine, et al., "Sequence and promoter analysis of the highly expressed TEF gene of the filamentous fungus Ashbya gossypii", Mol Gen Genet, 1994, 242, pp. 263-271.

*Primary Examiner* — Nancy T Vogel
(74) *Attorney, Agent, or Firm* — John D. Fado; David L. Marks

(57) ABSTRACT

Disclosed are isolated nucleic acid molecules that have promoter activity specific to xylose. The synthetic promoters, SEQ ID NO: 2, SEQ ID NO: 3, and SEQ ID NO: 4, promote the expression of a coding region of interest in transformed yeast cells.

10 Claims, 6 Drawing Sheets

SYNTHETIC PROMOTER FOR XYLOSE-REGULATED GENE EXPRESSION

FIELD OF THE INVENTION

This invention relates to synthetic promoter regions derived from the *Ashbya gossypii* TEF promoter that are useful for gene expression in yeast. More specifically, the synthetic promoter controls gene expression in response to xylose availability.

BACKGROUND OF INVENTION

Xylose is the second most abundant sugar in nature (Saha B C: Hemicellulose bioconversion. J Ind Microbiol Biotechnol 2003, 30:279-291), however yeast strains such as *Saccharomyces* are unable to metabolize xylose. A technical challenge to enable and enhance yeast capability in utilization of pentose sugars such as xylose and arabinose harbored in biomass is to engineer yeast stains that can metabolize those sugars.

Genetic engineering efforts have been made to improve xylose utilization by overexpressing genes encoding pentose phosphate pathway (PPP) enzymes to enhance xylose flux into central carbon metabolism. For native *S. cerevisiae*, there are no xylose-specific transporters available and xylose uptake is via certain hexose transporters such as Hxt4, Hxt5, Hxt7, and Gal2. Recently, several heterologous sugar transporter genes possessing xylose transport functions have been expressed in recombinant *S. cerevisiae* such as SUT1, XUT1 or XUT3 from *S. stipitis*, At5g59250 and At5g17010 from *A. thaliana*, An25 from *N. crassa*, DEHA0D02167 and XylHP from *D. hansenii*, and symporters GXS1 and GXF1 genes from *C. intermedia*. Improvement of xylose utilization by such efforts was observed but a satisfactory level has not been reached.

While there has been focus on engineering yeast strains that metabolize xylose as a sugar source, the environment yeast operate have both xylose and glucose as part of the batch. For *S. cerevisiae* strains, uncontrolled, high-level expression of many genes required for xylose fermentation can be detrimental to cell growth and fermentation (Id.) Additionally, certain genes required for efficient xylose fermentation negatively affect glucose fermentation (Meinander N Q, et al., Fermentation of xylose/glucose mixtures by metabolically engineered *Saccharomyces cerevisiae* strains expressing XYL1 and XYL2 from *Pichia stipitis* with and without overexpression of TAL1. Bioresource Technol 1999, 68:79-87).

Recombinant production of any heterologous protein is generally accomplished by constructing an expression cassette in which the DNA coding for the protein of interest is placed under the control of a promoter suitable for the host cell. The expression cassette is then introduced into the host cell (i.e., usually by plasmid-mediated transformation or targeted integration into the host genome) and production of the heterologous protein is achieved by culturing the transformed host cell under conditions necessary for the proper function of the promoter contained within the expression cassette. Thus, the development of new host cells (e.g., transformed yeast) for recombinant production of proteins generally requires the availability of promoters that are suitable for controlling the expression of a protein of interest in the host cell.

While there are promoters that have been isolated from yeast cells that are useful in heterologous gene expression in yeast, most of these promoters provide constitutive gene expression. There are fewer inducible promoters available from *S. cerevisiae* for regulating gene expression and none of these are regulated by xylose. Thus, there is a need to develop a promoter that controls gene expression in response to xylose availability. Such an induced promoter would ensure efficient metabolism energy for the yeast cell without the cell growth and fermentation disadvantages stemming from unregulated, high-level expression, of multiple genes.

BRIEF SUMMARY OF THE INVENTION

Disclosed herein is an isolated nucleic acid molecule that has promoter activity specific to xylose and that comprises a DNA sequence selected from the group consisting of SEQ ID NO: 2, SEQ ID NO: 3, or SEQ ID NO: 4, wherein said isolated nucleic acid molecule is operatively linked to at least one heterologous nucleic acid sequence of interest. In one embodiment of the invention, a vector comprises the DNA sequence of SEQ ID NO: 2, SEQ ID NO: 3, or SEQ ID NO: 4. In another embodiment of the invention, a cell comprises a vector having the DNA sequence of SEQ ID NO: 2, SEQ ID NO: 3, or SEQ ID NO: 4. In yet another embodiment of the invention, the vector is stably integrated into the genome of the cell.

Disclosed herein is a method for expressing a coding region of interest in a transformed yeast cell comprising: a) providing a transformed yeast cell having a recombinant construct, wherein the recombinant construct comprises: (1) a promoter region comprising SEQ ID NO: 2, SEQ ID NO: 3, or SEQ ID NO: 4, and (2) a coding region of interest which is expressible in the yeast cell; wherein the promoter region is operably linked to the coding region of interest; and b) growing the transformed yeast cell of step (a) under conditions whereby the recombinant construct of step (a) is expressed. In one embodiment of the method, the yeast cell is a member of a genus selected from the group consisting of *Saccharomyes, Kluyveromyces, Candida, Scheffersomyces, Spathaspora, Yarrowia, Schizosaccharomyces, Zygosaccharomyces, Brettanomyces, Debaryomyces, Schwanniomyces, Pachysolen, Torulaspora, Hansenula, Pichia*. In yet another embodiment of the method, the coding region of interest encodes a polypeptide, wherein the polypeptide is selected from the group consisting of: xylanases, xylose reductases, xylose dehydrogenases, xylitol dehydrogenases, xylulokinases, xylose transporters, glucose transporters, galactose transporters, myo-inositol transporters, xylose isomerases, transhydrogenases, NADH kinases, NADP-dependent d-glyceraldehyde-3-phosphate dehydrogenases, transketolases, transaldolases, glucose-6-phosphated dehydrogenases, ribulose-5-phosphate isomerase, ribulose-5-phosphate epimerases, phosphoglucose isomerases, alcohol dehydrogenases, aldehyde dehydrogenases, 2-pyrone synthases, beta-xylosidases, acetyl-CoA synthases, acetyl-CoA carboxylase, phosphoketolases, acetate kinases, transcription factors, and phosphotransacetylases.

Also disclosed is a transformed yeast comprising a promoter and a heterologous gene encoding a protein, wherein the promoter comprises a polynucleotide of SEQ ID NO: 2, SEQ ID NO: 3, or SEQ ID NO: 4, wherein the polynucleotide is capable of activating expression of a gene in a yeast cell. In one embodiment of the invention, the transformed yeast having the promoter is operably linked to the nucleic acid sequence. In yet another embodiment of the invention, the transformed yeast is a *Saccharomyes cerevisiae, Kluyveromyces, Candida, Scheffersomyces, Spathaspora,*

Yarrowia, Schizosaccharomyces, Zygosaccharomyces, Brettanomyces, Debaryomyces, Schwanniomyces, Pachysolen, Torulaspora, Hansenula, or Pichia.

BRIEF DESCRIPTION OF THE DRAWING

The present invention together with the disclosed embodiments may best be understood from the following detailed description of the drawings, wherein.

BRIEF DESCRIPTION OF THE SEQUENCES

Figure 1A:
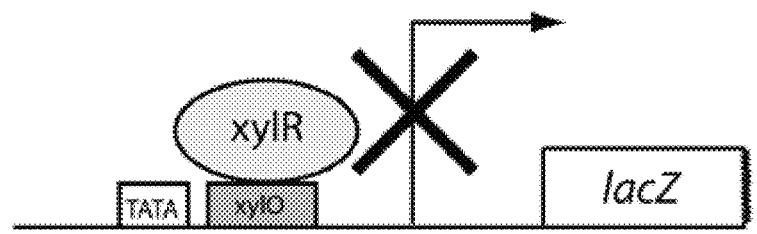
FIG. 1A depicts XylR binding to a xylO sequence and inhibiting transcription in the absence of xylose.

SEQ ID NO: 1 is a synthetic promoter:

```
GAGCTCAAGCTTGCCTCGTCCCGCCGGGTCACCCGGCCAGCGACATGGAG
GCCCAGAATACCCTCCTTGACAGTCTTGACGTGCGCAGCTCAGGGGCATG
ATGTGACTGTCGCCCGTACATTTAGCCCATACATCCCCATGTATAATCAT
TTGCATCCATACATTTTGATGGCCGCACGGCGCGAACGAAAAATTACGGC
TCCTCGCTGCAGACCTGCGAGCAGGGAAACGCTCCCCTCACAGACGCGTT
GAATTGTCCCCACGCCGCGCCCCTGTAGAGAAATATAAAAGGTTAGGATT
TGCCACTGAGGTTCTTCTTTCACATACTTCCTTTTAAAATCTTGCTAGGA
TACAGTTCTCACATCACATCCGAACATAAACAAAAACTAGT.
```

SEQ ID NO: 2 is a synthetic promoter:

```
GAGCTCAAGCTTGCCTCGTCCCGCCGGGTCACCCGGCCAGCGACATGGAG
GCCCAGAATACCCTCCTTGACAGTCTTGACGTGCGCAGCTCAGGGGCATG
ATGTGACTGTCGCCCGTACATTTAGCCCATACATCCCCATGTATAATCAT
TTGCATCCATACATTTTGATGGCCGCACGGCGCGAACGAAAAATTACGGC
TCCTCGCTGCAGACCTGCGAGCAGGGAAACGCTCCCCTCACAGACGCGTT
GAATTGTCCCCACGCCGCGCCCCTGTAGAGAAATATAAAACATGTTAGCG
CTACCAAGTGGTTCTTCTTTCACATACTTCCTTTTAAAATCTTGCTAGGA
TACAGTTCTCACATCACATCCGAACATAAACAAAAACTAGT.
```

SEQ ID NO: 3 is a synthetic promoter:

```
GAGCTCAAGCTTGCCTCGTCCCGCCGGGTCACCCGGCCAGCGACATGGAG
GCCCAGAATACCCTCCTTGACAGTCTTGACGTGCGCAGCTCAGGGGCATG
ATGTGACTGTCGCCCGTACATTTAGCCCATACATCCCCATGTATAATCAT
TTGCATCCATACATTTTGATGGCCGCACGGCGCGAACGAAAAATTACGGC
TCCTCGCTGCAGACCTGCGAGCAGGGAAACGCTCCCCTCACAGACGCGTT
GAATTGTCCCACATGTTAGCGCTACCAAGTAAATATAAAACATGTTAGCG
CTACCAAGTGGTTCTTCTTTCACATACTTCCTTTTAAAATCTTGCTAGGA
TACAGTTCTCACATCACATCCGAACATAAACAAAAACTAGT.
```

SEQ ID NO: 4 is a synthetic promoter:

```
GAGCTCAAGCTTGCCTCGTCCCGCCGGGTCACCCGGCCAGCGACATGGAG
GCCCAGAATACCCTCCTTGACAGTCTTGACGTGCGCAGCTCAGGGGCATG
ATGTGACTGTCGCCCGTACATTTAGCCCATACATCCCCATGTATAATCAT
TTGCATCCATACATTTTGATGGCCGCACGGCGCGAACGAAAAATTACGGC
TCCTCGCTGCAGACCTGCGAGCAGGGAAACGCTCCCCTCACAGACGCGTT
GAATTGTCCCCACGCCGCGCCCCTGTAGAGAAATATAAAACATGTTAGCG
CTACCAAGTACATGTTAGCGCTACCAAGTCCTTTTAAAATCTTGCTAGGA
TACAGTTCTCACATCACATCCGAACATAAACAAAAACTAGT.
```

SEQ ID NO: 5 is a nucleotide sequence of a nuclear localization signal:

```
ATGCCCAAGAAGAAAAGGAAAGTT.
```

SEQ ID NO: 6 is a gene that encodes a sequence-specific DNA binding protein that is optimized for expression in Saccharomyces cerevisiae:

```
ATGAATCAACCAGTAGAAAGACAGCGTAGGAGAACTACTCAAAGTGCTAC
AATTCGTGACGTAGCTGCAAGAGCAGGTGTCTCTCCTATGACAGTCTCAC
GTGTAATCAATAGAGAGTCCACAGTTAAAGAGGAAACTAGACAGTTGGTT
GAAAAGGCAATAGCCGACCTTAACTATGCTCCTAATCCTGCAGCCAGATC
TTTGGCAGGTAGTGCCCCTTTTAGAATTGGCTTACTGTACGATAATCCTT
CAACTGGCTACCTTTCTGAATTTCTAGTTGGTGCCTTAGATGAATCAAGT
AGAACCGGTGCTCAAATTGTTATCGAGAAATGTGCTGAACCAGAATTAGC
CAGAGCTACACTTGCTAGATTGTTGAAAACTGGAGTTGATGGACTTATCT
TACCTCCACCATTATGCGAATCTCCAGAAGTTCTGGCCGAGATAAGAGCC
```

-continued

```
GCAGGAGCTGCCGCTGTCGCAGTGGCACCTGGTACAGCTTCTGCCGACAT

GGCTACTATTAGAATCGACAACGAAGCAGCTGCATTTGAGTTGACCCAGC

ATTTGATTGGCTTGGGTCACAAAAGATTCGGATTCATTAAGGGTCATCCA

AATCAAACCGTGTCTCAACAAAGGCTTGATGGGTTTATGACTGCTCTTAA

GGCTGCAGGGATCCCACAAGAGAATATCAGAGTGGAACAAGGTTACTTCA

CATATCGTTCAGGTCTAGAAGCTGCAGAGAGACTACTAGCAGCCGAACCT

AGGCCAACTGCCATCTTCGCTGCTAACGATGATATGGCAGCTGCAACAGC

AGGCGTAGCACATAGACTAGGCTTGGATGTACCAGGCGACGTGTCTATAG

TGGGATTTGATGATACTTCCATAGCTGATAACATTTGGCCACCATTAACA

ACAGTTCACCAACCAATTGCCGCTATGGCCAGAGCCGCTGTTGATCTGGT

TCTAGAAGAGATCAGAAGGCATAGAGATGGTGGTGGCGAACCTAGACAAT

TGATGCATCCACACACTCTGATCGTTAGAGACTCCTCAGGCCCTGCTGGA

GTCTAA.
```

SEQ ID NO: 7 is a gene that encodes a sequence specific DNA binding protein that is optimized for expression in *Saccharomyces cerevisiae* and connected to a nuclear localization signal (SEQ ID NO 5):

```
ATGCCCAAGAAGAAAGGAAAGTTAATCAACCAGTAGAAAGACAGCGTAG

GAGAACTACTCAAAGTGCTACAATTCGTGACGTAGCTGCAAGAGCAGGTG

TCTCTCCTATGACAGTCTCACGTGTAATCAATAGAGAGTCCACAGTTAAA

GAGGAAACTAGACAGTTGGTTGAAAAGGCAATAGCCGACCTTAACTATGC

TCCTAATCCTGCAGCCAGATCTTTGGCAGGTAGTGCCCCTTTTAGAATTG

GCTTACTGTACGATAATCCTTCAACTGGCTACCTTTCTGAATTTCTAGTT

GGTGCCTTAGATGAATCAAGTAGAACCGGTGCTCAAATTGTTATCGAGAA

ATGTGCTGAACCAGAATTAGCCAGAGCTACACTTGCTAGATTGTTGAAAA

CTGGAGTTGATGGACTTATCTTACCTCCACCATTATGCGAATCTCCAGAA

GTTCTGGCCGAGATAAGAGCCGCAGGAGCTGCCGCTGTCGCAGTGGCACC

TGGTACAGCTTCTGCCGACATGGCTACTATTAGAATCGACAACGAAGCAG

CTGCATTTGAGTTGACCCAGCATTTGATTGGCTTGGGTCACAAAAGATTC

GGATTCATTAAGGGTCATCCAAATCAAACCGTGTCTCAACAAAGGCTTGA

TGGGTTTATGACTGCTCTTAAGGCTGCAGGGATCCCACAAGAGAATATCA

GAGTGGAACAAGGTTACTTCACATATCGTTCAGGTCTAGAAGCTGCAGAG

AGACTACTAGCAGCCGAACCTAGGCCAACTGCCATCTTCGCTGCTAACGA

TGATATGGCAGCTGCAACAGCAGGCGTAGCACATAGACTAGGCTTGGATG

TACCAGGCGACGTGTCTATAGTGGGATTTGATGATACTTCCATAGCTGAT

AACATTTGGCCACCATTAACAACAGTTCACCAACCAATTGCCGCTATGGC

CAGAGCCGCTGTTGATCTGGTTCTAGAAGAGATCAGAAGGCATAGAGATG

GTGGTGGCGAACCTAGACAATTGATGCATCCACACACTCTGATCGTTAGA

GACTCCTCAGGCCCTGCTGGAGTCTAA.
```

SEQ ID NO: 8 is a gene that encodes a sequence specific DNA binding protein that is optimized for expression in *Saccharomyces cerevisiae* and connected to a nuclear localization signal (SEQ ID NO 5) and the *S. cerevisiae* SSN6 gene:

```
ATGCCCAAGAAGAAAGGAAAGTTAATCAACCAGTAGAAAGACAGCGTAG

GAGAACTACTCAAAGTGCTACAATTCGTGACGTAGCTGCAAGAGCAGGTG

TCTCTCCTATGACAGTCTCACGTGTAATCAATAGAGAGTCCACAGTTAAA

GAGGAAACTAGACAGTTGGTTGAAAAGGCAATAGCCGACCTTAACTATGC

TCCTAATCCTGCAGCCAGATCTTTGGCAGGTAGTGCCCCTTTTAGAATTG

GCTTACTGTACGATAATCCTTCAACTGGCTACCTTTCTGAATTTCTAGTT

GGTGCCTTAGATGAATCAAGTAGAACCGGTGCTCAAATTGTTATCGAGAA

ATGTGCTGAACCAGAATTAGCCAGAGCTACACTTGCTAGATTGTTGAAAA

CTGGAGTTGATGGACTTATCTTACCTCCACCATTATGCGAATCTCCAGAA

GTTCTGGCCGAGATAAGAGCCGCAGGAGCTGCCGCTGTCGCAGTGGCACC

TGGTACAGCTTCTGCCGACATGGCTACTATTAGAATCGACAACGAAGCAG

CTGCATTTGAGTTGACCCAGCATTTGATTGGCTTGGGTCACAAAAGATTC

GGATTCATTAAGGGTCATCCAAATCAAACCGTGTCTCAACAAAGGCTTGA

TGGGTTTATGACTGCTCTTAAGGCTGCAGGGATCCCACAAGAGAATATCA

GAGTGGAACAAGGTTACTTCACATATCGTTCAGGTCTAGAAGCTGCAGAG

AGACTACTAGCAGCCGAACCTAGGCCAACTGCCATCTTCGCTGCTAACGA

TGATATGGCAGCTGCAACAGCAGGCGTAGCACATAGACTAGGCTTGGATG

TACCAGGCGACGTGTCTATAGTGGGATTTGATGATACTTCCATAGCTGAT

AACATTTGGCCACCATTAACAACAGTTCACCAACCAATTGCCGCTATGGC

CAGAGCCGCTGTTGATCTGGTTCTAGAAGAGATCAGAAGGCATAGAGATG

GTGGTGGCGAACCTAGACAATTGATGCATCCACACACTCTGATCGTTAGA

GACTCCTCAGGCCCTGCTGGAGTCGGTTCCGGAGGTGGAGGTTCTATGAA

TCCGGGCGGTGAACAAACAATAATGGAACAACCCGCTCAACAGCAACAAC

AACAGCAACAACAACAGCAGCAACAGCAACAGCAGGCAGCAGTTCCTCAG

CAGCCACTCGACCCATTAACACAATCAACTGCGGAAACTTGGCTCTCCAT

TGCTTCTTTGGCAGAAACCCTTGGTGATGGCGACAGGGCCGCAATGGCAT

ATGACGCCACTTTACAGTTCAATCCCTCATCTGCAAAGGCTTTAACATCT

TTGGCTCACTTGTACCGTTCCAGAGACATGTTCCAAAGAGCTGCAGAATT

ATATGAAAGAGCACTTTTGGTAAATCCCGAACTATCAGATGTGTGGGCTA

CTTTAGGTCATTGTTATCTGATGCTGGATGATCTGCAAAGAGCTTACAAT

GCCTATCAACAGGCTCTCTACCACCTCAGTAATCCCAACGTACCGAAATT

ATGGCATGGAATCGGCATTCTTTATGACAGATATGGTTCGCTCGACTATG

CCGAAGAAGCTTTTGCCAAAGTTTTGGAATTGGACCCTCATTTTGAAAAG

GCAAACGAAATTTACTTCAGACTAGGTATTATTTATAAACATCAGGGTAA

ATGGTCTCAAGCTTTGGAATGCTTCAGATACATTCTCCCTCAACCTCCTG

CTCCCTTGCAGGAGTGGGACATATGGTTTCAGTTGGGTAGTGTTTTGGAG

AGTATGGGAGAGTGGCAAGGTGCGAAGGAAGCCTACGAGCATGTCTTGGC
```

-continued

```
TCAAAATCAACATCATGCCAAAGTATTACAACAATTAGGTTGTCTTTACG

GTATGAGTAACGTACAATTTTATGACCCTCAAAAGGCATTGGATTATCTT

CTAAAGTCGTTAGAAGCAGATCCCTCCGATGCCACTACATGGTACCATCT

CGGTAGAGTGCATATGATTAGAACAGATTATACTGCCGCATATGATGCTT

TCCAACAAGCTGTTAATAGAGATTCAAGAAACCCTATCTTTTGGTGCTCA

ATCGGTGTTTTATATTACCAAATTTCTCAATACAGAGACGCCTTAGACGC

GTACACAAGAGCCATAAGATTAAATCCTTATATTAGTGAAGTTTGGTACG

ATCTAGGTACTCTTTACGAAACTTGTAACAACCAATTATCTGACGCCCTT

GATGCGTATAAGCAAGCTGCAAGACTGGACGTAAATAATGTTCACATAAG

AGAAAGATTAGAAGCTTTAACAAAGCAGTTAGAAAACCCAGGCAATATAA

ACAAATCGAACGGTGCGCCAACGAATGCCTCTCCTGCCCCACCTCCTGTG

ATTTTACAACCTACCTTACAACCTAATGATCAAGGAAATCCTTTGAACAC

TAGAATTTCAGCCCAATCTGCCAATGCTACTGCTTCAATGGTACAACAAC

AGCATCCTGCTCAACAAACGCCTATTAACTCTTCTGCAACAATGTACAGT

AATGGAGCTTCCCCTCAATTACAAGCTCAAGCTCAAGCTCAAGCTCAAGC

ACAAGCTCAAGCACAAGCACAAGCTCAAGCACAAGCACAAGCACAAGCGC

AAGCACAAGCACAGGCGCAAGCACAGGCACAAGCACAAGCACAAGCACAA

GCACATGCACAAGCGCAAGCACAAGCACAAGCACAGGCACAAGCACAAGC

ACAGGCGCAGGCACAACAACAACAACAACAGCAACAACAACAACAAC

AACAACAACAACAACAACAACAACAACAACAACAACAACAACAACAGCAG

CAGCAATTACAGCCCCTACCAAGACAACAGCTGCAGCAAAAGGGAGTTTC

TGTGCAAATGTTAAATCCTCAACAAGGGCAACCATATATCACACAGCCAA

CAGTCATACAAGCTCACCAACTGCAACCATTTTCTACACAAGCTATGGAA

CATCCGCAAAGCTCTCAACTGCCACCTCAACAGCAACAACTACAATCTGT

TCAACATCCACAACAACTTCAAGGCCAGCCTCAAGCCCAAGCTCCCCAAC

CTTTAATCCAGCATAACGTGGAACAGAACGTTTTACCTCAAAAGAGATAC

ATGGAAGGTGCAATCCACACTTTAGTAGATGCCGCCGTATCCAGTAGCAC

CCACACAGAGAATAACACAAAGTCTCCTCGTCAACCAACCCATGCCATTC

CAACGCAAGCTCCCGCAACAGGAATAACGAACGCTGAACCACAGGTAAAG

AAGCAAAAGTTGAACTCTCCAAATTCAAACATCAACAAATTAGTAAATAC

TGCTACTTCCATTGAAGAAAATGCAAAATCTGAGGTGAGCAACCAATCGC

CAGCAGTAGTGGAGTCTAATACCAATAATACTTCACAAGAAGAAAAACCT

GTAAAAGCAAACTCAATACCTTCAGTAATTGGCGCACAGGAACCTCCACA

GGAAGCTAGTCCTGCTGAAGAAGCTACCAAAGCAGCTTCTGTTTCTCCTT

CTACAAAACCGCTTAATACGGAACCAGAGTCATCTAGTGTCCAACCAACT

GTATCATCAGAAAGTTCAACAACAAAAGCAAATGACCAAAGCACTGCTGA

GACCATAGAACTTTCTACTGCTACTGTTCCTGCAGAAGCAAGCCCTGTAG

AAGACGAAGTAAGACAGCATTCTAAAGAGGAAAACGGCACAACTGAAGCA

TCTGCACCTTCTACTGAAGAGGCGGAGCCAGCAGCTTCCAGAGATGCTGA

AAAACAACAAGATGAAACCGCTGCTACAACGATAACTGTAATCAAACCTA
```

-continued
```
CTTTGGAAACAATGGAAACAGTGAAAGAGGAGGCCAAAATGCGTGAGGAA

GAGCAAACATCTCAAGAAAAATCCCCACAGGAGAACACACTTCCAAGAGA

AAATGTAGTAAGGCAAGTGGAAGAAGATGAAAACTACGACGACTAA.
```

SEQ ID NO: 9 is a synthetic promoter:

```
GAGCTCAAGCTTGCCTCGTCCCGCCGGGTCACCCGGCCAGCGACATGGAG

GCCCAGAATACCCTCCTTGACAGTCTTGACGTGCGCAGCTCAGGGGCATG

ATGTGACTGTCGCCCGTACATTTAGCCCATACATCACATGTTAGCGCTAC

CAAGTTGCATCCATACATTTTGATGGCCGCACGGCGCGAACGAAAAATTA

CGGCTCCTCGCTGCAGACCTGCGAGCAGGGAAACGCTCCCCTCACAGACG

CGTTGAATTGTCCCCACGCCGCGCCCCTGTAGAGAAATATAAAAGGTTAG

GATTTGCCACTGAGGTTCTTCTTTCACATACTTCCTTTTAAAATCTTGCT

AGGATACAGTTCTCACATCACATCCGAACATAAACAAAAACTAGT.
```

SEQ ID NO: 10 is a synthetic promoter:

```
GAGCTCAAGCTTGCCTCGTCCCGCCGGGTCACCCGGCCAGCGACATGGAG

GCCCAGAATACCCTCCTTGACAGTCTTGACGTGCGCAGCTCAGGGGCATG

ATGTGACTGTCGCCCGTACATTTAGCCCATACATCACATGTTAGCGCTAC

CAAGTTGCATCCATACATTTTACATGTTAGCGCTACCAAGTGAAAAATTA

CGGCTCCTCGCTGCAGACCTGCGAGCAGGGAAACGCTCCCCTCACAGACG

CGTTGAATTGTCCCCACGCCGCGCCCCTGTAGAGAAATATAAAAGGTTAG

GATTTGCCACTGAGGTTCTTCTTTCACATACTTCCTTTTAAAATCTTGCT

AGGATACAGTTCTCACATCACATCCGAACATAAACAAAAACTAGT.
```

SEQ ID NO: 11 is a synthetic promoter:

```
GAGCTCAAGCTTGCCTCGTCCCGCCGGGTCACCCGGCCAGCGACATGGAG

GCCCAGAATACCCTCCTTGACAGTCTTGACGTGCGCAGCTCAGGGGCATG

ATGTGACTGTCGCCCGTACATTTAGCCCATACATCACATGTTAGCGCTAC

CAAGTTGCATCCATACATTTTACATGTTAGCGCTACCAAGTGAAAAATTA

CGGCTCCTCGCTGCAGACCTGCGAGCAGGGAAACGCTCCCCTCACAGACG

CGTTGAATTGTCCCCACGCCGCGCCCCTGTAGAGAAATATAAACATGTT

AGCGCTACCAAGTACATGTTAGCGCTACCAAGTCCTTTTAAAATCTTGCT

AGGATACAGTTCTCACATCACATCCGAACATAAACAAAAACTAGT.
```

SEQ ID NO: 12 is a synthetic sequence:

```
ACATGTTAGCGCTACCAAGT.
```

DETAILED DESCRIPTION OF THE INVENTION

Definitions

As used in the specification and claims, the singular form "a", "an" and "the" include plural references unless the context clearly dictates otherwise. For example, the term "a cell" includes a plurality of cells, including mixtures thereof.

As used herein, the term "cloning" refers to the selection and propagation of (a) genetic material from a single individual, (b) a vector containing one gene or gene fragment, or (c) a single organism containing one such gene or gene fragment.

As used herein, the term "vector" or "plasmid" each refer to a non-chromosomal (episomal) double-stranded DNA sequence comprising an intact "replicon" such that the vector or plasmid is replicated in a host cell. When the plasmid is placed within a unicellular organism, the characteristics of that organism may be changed or transformed as a result of the DNA of the plasmid. A cell transformed by a plasmid is called a "transformant".

As used herein, the term "cloning vector" refers to a plasmid, virus, retrovirus, bacteriophage, cosmid, artificial chromosome (bacterial or yeast), or nucleic acid sequence which is able to replicate in a host cell, characterized by one or a small number of restriction endonuclease recognition sites at which the sequence may be cut in a predetermined fashion, and which may contain an optional marker suitable for use in the identification of transformed cells, e.g., tetracycline resistance or ampicillin resistance. A cloning vector may or may not possess the features necessary for it to operate as an expression vector.

As used herein, the term "codon" refers to a DNA sequence of three nucleotides (a triplet) which codes (through mRNA) for an amino acid, a translational start signal, or a translational termination signal. For example, the nucleotide triplets TTA, TTG, CTT, CTC, CTA, and CTG encode for the amino acid leucine, while TAG, TAA, and TGA are translational stop signals, and ATG is a translational start signal.

As used herein, the term "DNA coding sequence" refers to a DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, prokaryotic sequences and cDNA from eukaryotic mRNA. A polyadenylation signal and transcription termination sequence will usually be located 3' to the coding sequence.

As used herein, the term "DNA construct" refers to an artificially constructed (i.e., non-naturally occurring) DNA molecules useful for introducing DNA into host cells, including chimeric genes, expression cassettes, and vectors.

As used herein, the term "DNA sequence" refers a linear series of nucleotides connected one to the other by phosphodiester bonds between the 3' and 5' carbons of adjacent pentoses.

As used herein, the term "expression" refers to the process undergone by a structural gene to produce a polypeptide. Expression requires transcription of DNA, post-transcriptional modification of the initial RNA transcript, and translation of RNA.

As used herein, the term "expression cassette" refers to a chimeric nucleic acid construct, typically generated recombinantly or synthetically, which comprises a series of specified nucleic acid elements that permit transcription of a particular nucleic acid in a host cell. In an exemplary embodiment, an expression cassette comprises a heterologous nucleic acid to be transcribed, operably linked to a promoter. Typically, an expression cassette is part of an expression vector.

As used herein, the term "operably linked", "operably encodes", or "operably associated" each refer to the functional linkage between a promoter and nucleic acid sequence, wherein the promoter initiates transcription of RNA corresponding to the DNA sequence. A heterologous DNA sequence is "operatively associated" with the promoter in a cell when RNA polymerase which binds the promoter sequence transcribes the coding sequence into mRNA which is then in turn translated into the protein encoded by the coding sequence.

As used herein, the term "expression control sequence" refers to expression control sequences that are DNA sequences involved in any way in the control of transcription or translation and must include a promoter. Suitable expression control sequences and methods of making and using them are well known in the art.

As used herein, the term "expression vector" refers a nucleic acid which comprises an expression cassette and which is capable of replicating in a selected host cell or organism. An expression vector may be a plasmid, virus, retrovirus, bacteriophage, cosmid, artificial chromosome (bacterial or yeast), or nucleic acid sequence which is able to replicate in a host cell, characterized by a restriction endonuclease recognition site at which the sequence may be cut in a predetermined fashion for the insertion of a heterologous DNA sequence. An expression vector may include the promoter positioned upstream of the site at which the sequence is cut for the insertion of the heterologous DNA sequence, the recognition site being selected so that the promoter will be operatively associated with the heterologous DNA sequence. A heterologous DNA sequence is "operatively associated" with the promoter in a cell when RNA polymerase which binds the promoter sequence transcribes the coding sequence into mRNA which is then in turn translated into the protein encoded by the coding sequence.

As used herein, the term "gene" refers to a segment of DNA which encodes a specific protein or polypeptide, or RNA.

As used herein, the term "genome" refers to the entire DNA of an organism. It includes, among other things, the structural genes encoding for the polypeptides of the substance, as well as operator, promoter and ribosome binding and interaction sequences.

As used herein, the term "heterologous DNA" refers to a DNA sequence inserted within or connected to another DNA sequence which codes for polypeptides not coded for in nature by the DNA sequence to which it is joined. Allelic variations or naturally occurring mutational events do not give rise to a heterologous DNA sequence as defined herein.

As used herein, the term "hybridization" refers to the pairing together or annealing of single stranded regions of nucleic acids to form double-stranded molecules.

As used herein, the term "nucleotide" refers to a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. The base characterizes the nucleotide. The four DNA bases are adenine ("A"), guanine ("G"), cytosine ("C"), and thymine ("T"). The four RNA bases are A, G, C, and uracil ("U").

As used herein, the term "promoter" refers to a DNA sequence within a larger DNA sequence defining a site to which RNA polymerase may bind and initiate transcription. A promoter may include optional distal enhancer or repressor elements. The promoter may be either homologous, i.e., occurring naturally to direct the expression of the desired nucleic acid, or heterologous, i.e., occurring naturally to direct the expression of a nucleic acid derived from a gene other than the desired nucleic acid. A promoter may be constitutive or inducible. A constitutive promoter is a promoter that is active under most environmental and developmental conditions. An inducible promoter is a promoter that is active under environmental or developmental regulation, e.g., upregulation in response to xylose availability. Promoters may be derived in their entirety from a native gene, may comprise a segment or fragment of a native gene, or may be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. It is further understood that the same promoter may be differentially expressed in different tissues and/or differentially expressed under different conditions.

As used herein, the term "promoter activity" will refer to an assessment of the transcriptional efficiency of a promoter. This may, for instance, be determined directly by measurement of the amount of mRNA transcription from the promoter (e.g., by quantitative PCR or Northern blotting or primer extension methods) or indirectly by measuring the amount of gene product expressed from the promoter.

As used herein, the term "yeast" refers to a phylogenetically diverse grouping of single-celled fungi. Yeast do not form a specific taxonomic or phylogenetic grouping, but instead comprise a diverse assemblage of unicellular organisms that occur in the Ascomycotina and Basidiomycotina. Collectively, about 100 genera of yeast have been identified, comprising approximately 1,500 species (Kurtzman and Fell, *Yeast Systematics And Phylogeny: Implications Of Molecular Identification Methods For Studies In Ecology*. In C. A. Rosa and G. Peter, eds., *The Yeast Handbook*. Germany: Springer-Verlag Berlin Herdelberg, 2006). Yeast reproduce principally by budding (or fission) and derive energy from fermentation, via conversion of carbohydrates to ethanol and carbon dioxide. Examples of some yeast genera include, but are not limited to: *Saccharomyes, Kluyveromyces, Candida, Scheffersomyces, Spathaspora, Yarrowia, Schizosaccharomyces, Zygosaccharomyces, Brettanomyces, Debaryomyces, Schwanniomyces, Pachysolen, Torulaspora, Hansenula, Pichia.*

The disclosure herein teaches partial or complete nucleotide sequences containing one or more particular yeast promoters. The skilled artisan, having the benefit of the sequences as reported herein, may now use all or a substantial portion of the disclosed sequences for purposes known to those skilled in this art. Accordingly, the complete sequences as reported in the accompanying Sequence Listing, as well as substantial portions of those sequences as defined above, are encompassed in the present disclosure.

Standard recombinant DNA and molecular cloning techniques used herein are well known in the art and are described more fully in Sambrook, J., Fritsch, E. F. and Maniatis, T. Molecular Cloning: A Laboratory Manual; Cold Spring Harbor Laboratory Cold Spring Harbor, N.Y. (1989); by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience, Hoboken, N.J. (1987).

Materials Used

*Escherichia coli* strains DH10B, TOP10 (Invitrogen; Carlsbad, Calif., USA), NEB10β (NEB; Beverly, Mass., USA) were used for routine maintenance and preparation of plasmids and were grown in LB medium (Sambrook and Russell, 2001, *Molecular Cloning: A Laboratory Manual*. 3rd edn. Cold Spring Harbor, N.Y.: Cold Spring Harbor Laboratory Press). Plasmids and strains are listed in Table 1 and Table 2. Plasmid DNA was transformed into yeast cells using a standard lithium acetate method (Gietz and Woods, 2002, Transformation of yeasts by the lithium acetate/single-stranded carrier/polyethylene glycol method. *Methods Enzymol*, 350:87-96). Synthetic medium consisted of 6.7 g/L Difco yeast nitrogen base (YNB) (United States Biological; Marblehead, Mass., USA), and was supplemented with amino acids (Amberg, Burke et al., 2005, *Methods in Yeast Genetics: A Cold Spring Harbor Laboratory Course Manual*. 2005 edn. Cold Spring Harbor, N.Y.: Cold Spring Harbor Laboratory Press). For maintenance of plasmids, media was made without tryptophan or leucine as necessary for plasmid maintenance. Synthetic medium was filter sterilized. Sterile carbon sources were added separately.

TABLE 1

Plasmids used

| Plasmid | Description | |
|---|---|---|
| pRS414 | pBluescript ∥ SK+, TRP1, CEN6, ARSH4 | Christianson TW, et al., Multifunctional yeast high-copy-number shuttle vectors. Gene 1992, 110:119-122. |
| pRS415 | pBluescript ∥ SK+, LEU2, CEN6, ARSH4 | Gene 1992, 110:119-122. |
| pUC57 | Gene synthesis vector | (GenScript) |
| pJ201 | Cloning vector | (DNA2.0) |
| pRH164 | pRS414 + $P_{HXT7}$-MCS-$T_{HXT7}$ | Hector RE, et al., Engineering industrial *Saccharomyces cerevisiae* strains for xylose fermentation and comparison for switchgrass conversion. J Ind Microbiol |

TABLE 1-continued

Plasmids used

| Plasmid | Description | |
|---|---|---|
| | | Biotechnol 2011, 38:1193-1202. |
| pRH457 | pJ201 + C. crescentus xylR[a] | (DNA2.0) |
| pRH463 | pRH164 + C. crescentus xylR | This work |
| pRH467 | pRH164 + C. crescentus xylR with N-tremminal NLS added | This work |
| pRH482 | pCR2.1 + C. crescentus NLS-xylR-linker-SSN6 | This work |
| pRH483 | pRH164 + C. crescentus NLS-xylR-linker-SSN6 | This work |
| pRH499 | pUC57 + $P_{TEF}$ | (GenScript) |
| pRH500 | pUC57 + $P_{TEF\text{-}xylO1}$ | (GenScript) |
| pRH501 | pUC57 + $P_{TEF\text{-}xylO2\text{-}1}$ | (GenScript) |
| pRH502 | pUC57 + $P_{TEF\text{-}xylO2\text{-}2}$ | (GenScript) |
| pRH503 | pRS415 + $P_{TEF}$ – MCS – $T_{ADH1}$ | This work |
| pRH504 | pRS415 + $P_{TEF\text{-}xylO\ 1}$ – MCS – $T_{ADH1}$ | This work |
| pRH505 | pRS415 + $P_{TEF\text{-}xylO\ 2\text{-}1}$ – MCS – $T_{ADH1}$ | This work |
| pRH506 | pRS415 + $P_{TEF\text{-}xylO\ 2\text{-}2}$ – MCS – $T_{ADH1}$ | This work |
| pRH511 | pRS415 + $P_{TEF}$ – laCZ – $T_{ADH1}$ | This work |
| pRH512 | pRS415 + $P_{TEF\text{-}\ xylO\ 1}$ – lacZ – $T_{ADH1}$ | This work |
| pRH513 | pRS415 + $P_{TEF\text{-}\ xylO\ 2\text{-}1}$ – lacZ – $T_{ADH1}$ | This work |
| pRH514 | pRS415 + $P_{TEF\text{-}\ xylO\ 2\text{-}2}$ – lacZ – $T_{ADH1}$ | This work |
| pRH531 | pUC57 + $P_{TEF\text{-}UAS\text{-}xylO1}$ | (GenScript) |
| pRH532 | pUC57 + $P_{TEF\text{-}UAS\text{-}xylO2}$ | (GenScript) |
| pRH534 | pUC57 + $P_{TEF\text{-}xylO4}$ | (GenScript) |
| pRH546 | pRS415 + $P_{TEF\text{-}UAS\text{-}xylO\ 1}$ – lacZ – $T_{ADH1}$ | This work |
| pRH547 | pRS415 + $P_{TEF\text{-}UAS\text{-}xylO\ 2}$ – lacZ – $T_{ADH1}$ | This work |
| pRH549 | pRS415 + $P_{TEF\text{-}xylO\ 4}$ – lacZ – $T_{ADH1}$ | This work |

[a]The C. crescentus xylR gene used throughout this work was codon-optimized for expression in S. cerevisiae

TABLE 2

Microorganisms used

| Strain | Genotype (description) | Reference |
|---|---|---|
| CEN.PK2-1C | S. cerevisiae MATa ura3-52 trp1-289 leu2-3,112 his3Δ1 MAL2-8[C] SUC2 | Euroscarf |
| YRH1054 | CEN.PK2-1C [ pRH511 ($P_{TEF}$ – lacZ – $T_{ADH1}$) + pRS414] | This work |
| YRH1055 | CEN.PK2-1C [ pRH511 ($P_{TEF}$ – lacZ – $T_{ADH1}$) + pRH483 ($P_{HXT7}$–NLS-xylR-SSN6)] | This work |
| YRH1056 | CEN.PK2-1C [ pRH512 ($P_{TEF\text{-}xylO1}$-lacZ – $T_{ADH1}$) + pRS414] | This work |
| YRH1057 | CEN.PK2-1C [ pRH512 ($P_{TEF\text{-}\ xylO\ 1}$ – lacZ – $T_{ADH1}$) + pRH483 ($PP_{HXT7}$–NLS-xy1R-SSN6)] | This work |
| YRH1058 | CEN.PK2-1C [ pRH513 ($P_{TEF\text{-}\ xylO\ 2\text{-}1}$ – lacZ – $T_{ADH1}$) + pRS414] | This work |
| YRH1059 | CEN.PK2-1C [ pRH513 ($P_{TEF\text{-}\ xylO\ 2\text{-}1}$ – lacZ – $T_{ADH1}$) + pRH483 ($PP_{HXT7}$–NLS-xy1R-SSN6)] | This work |
| YRH1060 | CEN.PK2-1C [ pRH514 ($P_{TEF\text{-}\ xylO\ 2\text{-}2}$ – lacZ – $T_{ADH1}$) + pRS414] | This work |
| YRH1061 | CEN.PK2-1C [ pRH514 ($P_{TEF\text{-}\ xylO\ 2\text{-}2}$ – lacZ – $T_{ADH1}$) + pRH483 ($PP_{HXT7}$–NLS-xy1R-SSN6)] | This work |
| YRH1156 | CEN.PK2-1C [ pRH546 ($P_{TEF\text{-}UAS\text{-}xylO\ 1}$ – lacZ – $T_{ADH1}$) + pRS414] | This work |
| YRH1157 | CEN.PK2-1C [ pRH546 ($P_{TEF\text{-}UAS\text{-}\ xylO\ 1}$ – lacZ – $T_{ADH1}$) + pRH483 ($PP_{HXT7}$–NLS-xylR-SSN6)] | This work |
| YRH1158 | CEN.PK2-1C [ pRH547 ($P_{TEF\text{-}UAS\text{-}\ xylO\ 2}$ – lacZ -$T_{ADH1}$) + pRS414] | This work |
| YRH1159 | CEN.PK2-1C [ pRH547 ($P_{TEF\text{-}UAS\text{-}\ xylO\ 2}$ – lacZ -$T_{ADH1}$) + pRH483 ($PP_{HXT7}$–NLS-xylR-SSN6)] | This work |
| YRH1162 | CEN.PK2-1C [ pRH549 ($P_{TEF\text{-}\ xylO\ 4}$ – lacZ – $T_{ADH1}$) + pRS414] | This work |
| YRH1163 | CEN.PK2-1C [ pRH549 ($P_{TEF\text{-}\ xylO\ 4}$ – lacZ – $T_{ADH1}$) + pRH483 ($PP_{HXT7}$–NLS-xylR-SSN6)] | This work |
| YRH1227 | CEN.PK2-1C [ pRH514 ($P_{TEF\text{-}\ xylO\ 2\text{-}2}$ – lacZ – $T_{ADH1}$) + pRH467 ($PP_{HXT7}$ – NLS – xylR)] | This work |
| YRH1276 | CEN.PK2-1C [ pRH514 ($P_{TEF\text{-}\ xylO\ 2\text{-}2}$ – lacZ – $T_{ADH1}$) + pRH463 ($PP_{HXT7}$ – xylR)] | This work |

Example 1

Constructing Xylose Regulated Promoters

The constitutive promoter for the translation elongation factor 1α gene (TEF) from *Ashbya gossypii* (referred to as the AgTEF, or TEF, promoter) was modified to include DNA sequences that bind to a sequence-specific DNA-binding protein from *Caulobacter crescentus* (xylR). Furthermore, the nucleotide sequence of the AgTEF promoter was modified to 1) remove sequences that direct cleavage of the DNA by the restriction endonucleases EcoRI and BssHII, and 2)

remove an alternative TATA sequence to disable aberrant transcription initiation under conditions that inhibit transcription initiation from the main TATA sequence located at −108. To accomplish these goals the following nucleotides were changed: (1) T(→69)→C, (2) G(→127)→C, and C(−136)→G. A nucleotide sequence with these changes (SEQ ID NO: 1) was synthesized (GenScript USA, Piscataway, N.J.).

Figure 1B:
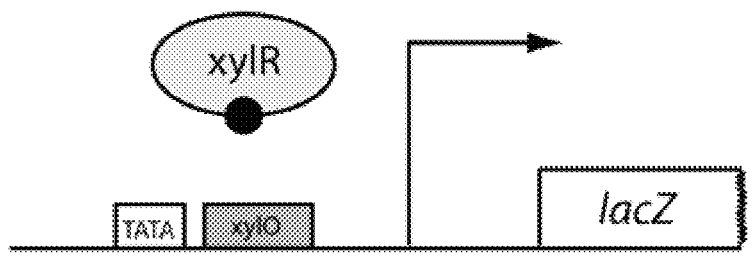
FIG. 1B depicts xyolse (•) is present and xylR dissociates from the xylO sequence allowing transcription.
Figure 1C:
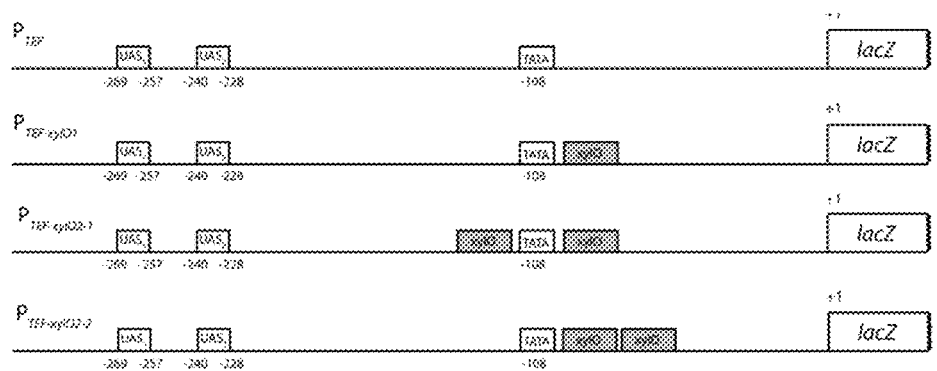
FIG. 1C depicts the location of xylO sequence with respect to the position of the TATA site and upstream activation sites (UAS$_{rpg1}$ and UAS$_{rpg2}$) of the Ashbya gossypii TEF promoter. Base position numbers are relative to the start codon of the β-galactosidase gene (lacZ).

To generate synthetic promoters capable of binding the xylR protein, 20 nucleotide segments located around the TATA sequence or upstream activation sequence elements were strategically replaced (FIG. 1 and FIG. 4) with the 20 nucleotide sequence (SEQ. ID. NO: 12 ACATGTTAGCGCTACCAAGT)

that has been demonstrated to interact with xylR in a xylose-dependent manner (Stephens C., et al., 2007, Regulation of D-xylose metabolism in *Caulobacter crescentus* by a LacI-type repressor. *J Bacteriol*, 189:8828-8834). Promoter variation $P_{TEF-xylO1}$ replaced nucleotides −83 to −102 (SEQ ID NO: 2). Promoter variation $P_{TEF-xylO2-1}$ replaced nucleotides −83 to −102 and −112 to −131 (SEQ ID NO: 3). Promoter variation $P_{TEF-xylO2-2}$ replaced nucleotides −63 to −82 and −83 to −102 (SEQ ID NO: 4). Promoter variation $P_{TEF-UAS-xylO\ 1}$ replaced nucleotides −241 to −256 (SEQ ID NO: 9). Promoter variation $P_{TEF-UAS-xylO\ 2}$ replaced nucleotides −215 to −234 and −241 to −256 (SEQ ID NO: 10). Promoter variation $P_{TEF-xylO\ 4}$ replaced nucleotides −63 to −82 and −83 to −102, −215 to −234, and −241 to −256 (SEQ ID NO: 11). These nucleotide sequences were synthesized (GenScript USA, Piscataway, N.J.). The nucleotide sequences were sub-cloned using restriction endonucleases SacI and SpeI and ligated into a vector that is able to replicate in *S. cerevisiae*. This vector also contained nucleotide sequences for additional restriction endonucleases for ease of adding heterologous genes that are operably linked to the promoter sequence. The vector also contained nucleotide sequence from the *S. cerevisiae* ADH1 gene 3' untranslated region (3' UTR) to direct the 3'-end cleavage and polyadenylation of the transcribed RNA that is necessary to generate a stable mRNA capable of efficient nucleocytoplasmic transport.

Figure 2:
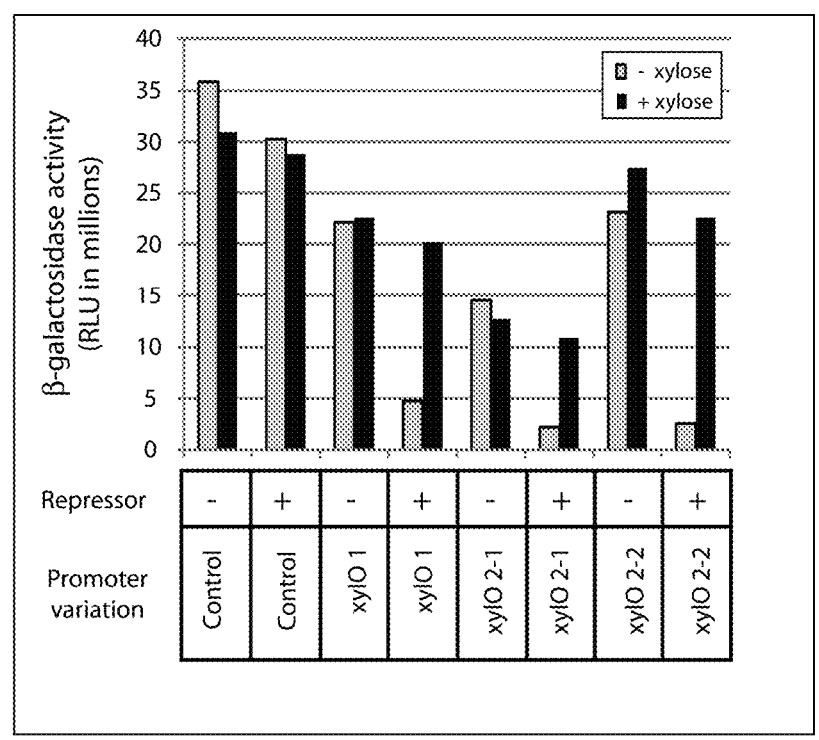
FIG. 2 is a graph of β-galactosidase activity measured for strains containing all promoter variations shown in FIG. 1. β-galactosidase activity is reported in Relative Light Units (RLUs) in millions. All variation shown were induced by xylose. The promoter variation xylO2-2, containing 2 repressor-binding sites 3' of the TATA element, yielded the greatest xylose induction.
Figure 3:
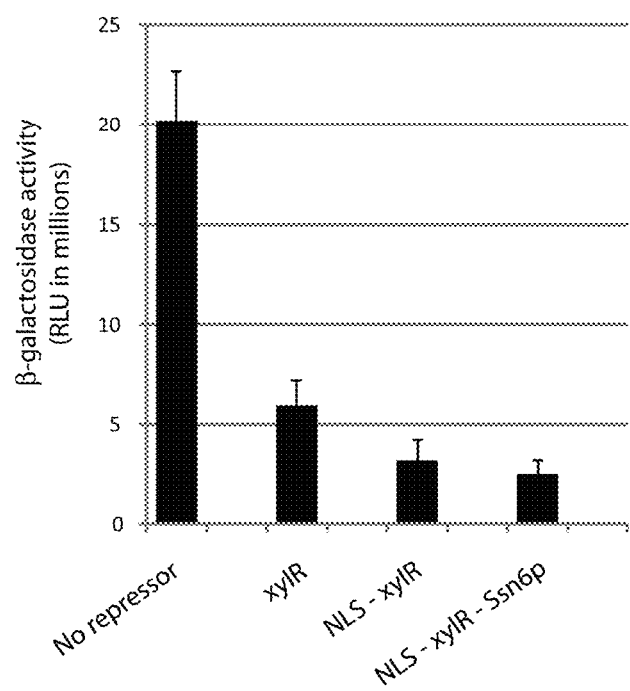
FIG. 3 is a graph comparing repressor variants and their β-galactosidase activity, measured in Relative Light Units (RLUs in millions). Addition of a nuclear localization signal (NLS) increased repression when xylose was not present. Additional fusion to a chromatin modifying protein, Ssn6p from Saccharomyces cerevisiae, resulted in a slight increase in repression.
Figure 4A:
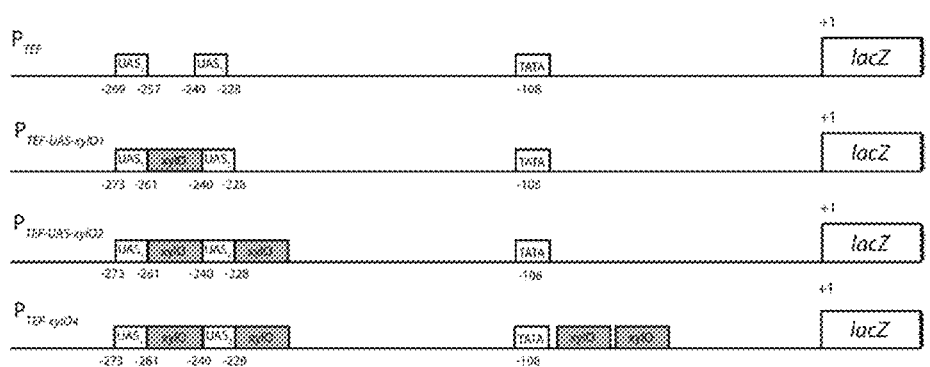
FIG. 4A depicts the location of xylO sequence with respect to the position of the TATA site and upstream activation sites (UAS$_{rpg1}$ and UAS$_{rpg2}$) of the Ashpya gossypii TEF promoter for variations of the promoter that were not inducible by xylose. Base position numbers are relative to the start codon.
Figure 4B:
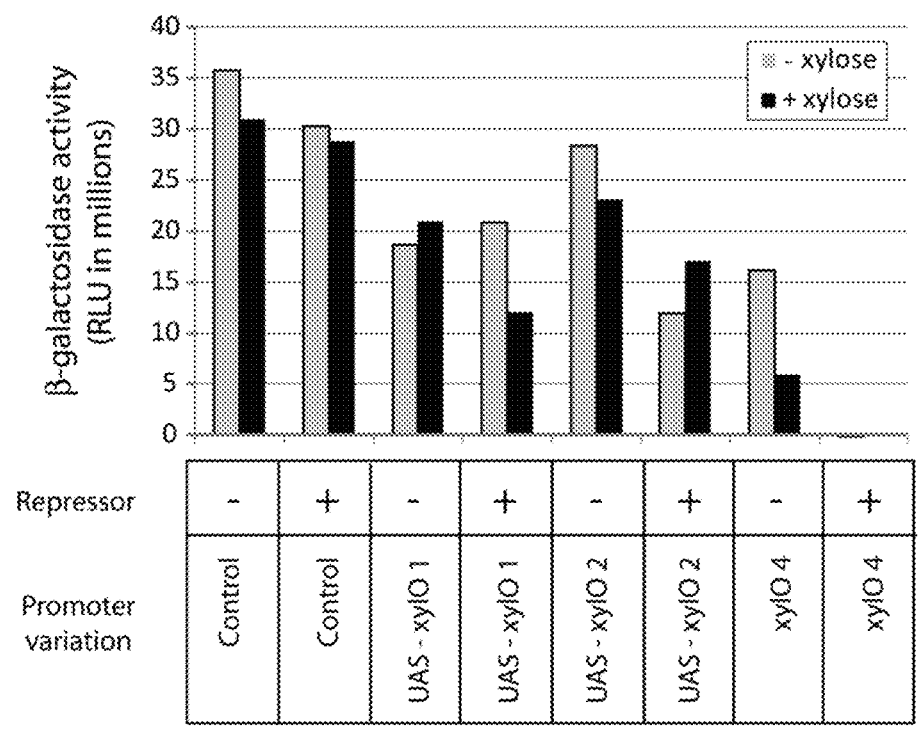
FIG. 4B is a graph of β-galactosidase (lacZ) activity measured for strains containing all promoter variations shown in FIG. 4 A. β-galactosidase activity is reported in Relative Light Units (RLUs) in millions.

In the absence of expression of the xylR repressor protein, each of the synthetic promoters provides constitutive expression (FIG. 2 and FIG. 4). Regulation by xylose is achieved by expression of the xylR protein. The gene for xylR from *C. crescentus* was codon-optimized for enhanced expression in *S. cerevisiae* and synthesized (DNA2.0, Menlo Park, Calif.)(SEQ ID NO: 6). This gene was operably linked to a constitutive promoter for expression in *S. cerevisiae*. Since bacterial proteins do not have to cross a nuclear membrane to interact with the DNA, one embodiment of this invention [SEQ ID NO: 7] has the xylR gene connected to a nuclear localization signal (NLS of SEQ ID NO: 5) to facilitate transport to the *S. cerevisiae* nucleus where the mode of transcription regulation is occurring. Another embodiment of the invention [SEQ ID NO: 8] comprises xylR connected to an NLS and the *S. cerevisiae* SSN6 gene. The Ssn6p protein is a chromatin modifying protein that mediates transcriptional repression. Addition of either the NLS or the NLS and SSN6 connected to xylR increased repression (FIG. 3).

Example 2

Transcriptional Activity Assay

Transcriptional activity of the promoter was assayed by operably linking the β-galacosidase gene (lacZ) to the promoter. The Beta-Glo Assay system (Promega; Madison, Wis., USA) was used to determine the level of transcriptional activity from promoter::lacZ constructs, essentially as reported in (Hector R. E., et al., 2009, The *Saccharomyces cerevisiae* YMR315W gene encodes an NADP(H)-specific oxidoreductase regulated by the transcription factor Stb5p in response to NADPH limitation, *N Biotechnol*, 26:171-180). Expression of the lacZ gene was assayed from cells grown in the presence or absence of xylose (FIG. 2, FIG. 3, and FIG. 4). Cells from cultures in log-phase (0.2 to 0.5 OD660) were diluted in fresh medium to a final OD660=0.004. Assays were started by adding 50 µL of diluted cells to 50 µL of Beta-Glo reagent, mixed thoroughly, and incubated at room temperature. The Beta-Glo reagent contains a detergent that lyses cells to release the β-galactosidase present. Using these conditions, activity measurements were stable from 60 to 120 min. All assays were performed in 96-well, opaque (white), flat-bottomed microtiter plates. At 60 min the samples were read using the luminescence mode of a SpectraMax M5 microplate reader (Molecular Devices; Sunnyvale, Calif., USA). β-galactosidase activities reported in the figures are based on the Relative Light Units (RLU) measured. Each assay was initiated using the same amount of cell mass to minimize variation due to differing cell concentrations.

To the extent that the term "includes" or "including" is employed in the detailed description or the claims, it is intended to be inclusive in a manner similar to the term "comprising" as that term is interpreted when employed as a transitional word in a claim. Furthermore, to the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995). Also, to the extent that the terms "in" or "into" are used in the specification or the claims, it is intended to additionally mean "on" or "onto." Furthermore, to the extent the term "connect" is used in the specification or claims, it is intended to mean not only "directly connected to," but also "indirectly connected to" such as connected through another component or components.

While the invention has been described with reference to details of the illustrated embodiment, these details are not intended to limit the scope of the invention as defined in the appended claims. All cited references and published patent applications cited in this application are incorporated herein by reference.

The embodiment of the invention in which exclusive property or privilege is claimed is defined as follows:

1. An isolated nucleic acid molecule that has promoter activity specific to xylose and that comprises a DNA sequence selected from the group consisting of SEQ ID NO: 2, SEQ ID NO: 3, or SEQ ID NO: 4, wherein said isolated nucleic acid molecule is operatively linked to at least one heterologous nucleic acid sequence of interest.

2. A vector comprising the isolated polynucleotide of claim 1.

3. A cell comprising the vector of claim 2.

4. The cell of claim 3, wherein the vector is stably integrated into the genome of the cell.

5. A vector comprising a promoter and a heterologous nucleic acid sequence, wherein the promoter comprises a polynucleotide of SEQ ID NO: 2, SEQ ID NO: 3, or SEQ ID NO: 4.

6. A method for expressing a coding region of interest in a transformed yeast cell comprising: a) providing a transformed yeast cell having a recombinant construct, wherein the recombinant construct comprises: (1) a promoter region comprising SEQ ID NO: 2, SEQ ID NO: 3, or SEQ ID NO: 4, and (2) a coding region of interest which is expressible in the yeast cell; wherein the promoter region is operably linked to the coding region of interest; and b) growing the transformed yeast cell of step (a) under conditions whereby the recombinant construct of step (a) is expressed.

7. The method of claim 6, wherein the yeast cell is a member of a genus selected from the group consisting of *Saccharomyes, Kluyveromyces, Candida, Scheffersomyces, Spathaspora, Yarrowia, Schizosaccharomyces, Zygosaccharomyces, Brettanomyces, Debaryomyces, Schwanniomyces, Pachysolen, Torulaspora, Hansenula,* or *Pichia*.

8. The method according to claim 6, wherein the coding region of interest encodes a polypeptide, wherein the polypeptide is selected from the group consisting of: xylanases, xylose reductases, xylose dehydrogenases, xylitol dehydrogenases, xylulokinases, xylose transporters, glucose transporters, galactose transporters, myoinositol transporters, xylose isomerases, transhydrogenases, NADH kinases, NADP-dependent d-glyceraldehyde-3-phosphate dehydrogenases, transketolases, transaldolases, glucose-6-phosphated dehydrogenases, ribulose-5-phosphate isomerase, ribulose-5-phosphate epimerases, phosphoglucose isomerases, alcohol dehydrogenases, aldehyde dehydrogenases, 2-pyrone synthases, beta-xylosidases, acetyl-CoA synthases, acetyl-CoA carboxylase, phosphoketolases, acetate kinases, transcription factors, and phosphotransacetylases.

9. A transformed yeast comprising a promoter and a heterologous gene encoding a protein, wherein the promoter comprises a polynucleotide of SEQ ID NO: 2, SEQ NO: 3, or SEQ ID NO: 4, wherein the polynucleotide is operably linked to said heterologous gene and causes transcription of said heterologous gene when xylose is available.

10. The transformed yeast of claim 9 wherein the transformed yeast is a *Saccharomyes cerevisiae, Kluyveromyces, Candida, Scheffersomyces, Spathaspora, Yarrowia, Schizosaccharomyces, Zygosaccharomyces, Brettanomyces, Debaryomyces, Schwanniomyces, Pachysolen, Torulaspora, Hansenula,* or *Pichia*.

* * * * *

SEQUENCE LISTING

<160> NUMBER OF SEQ ID NOS: 12

<210> SEQ ID NO 1
<211> LENGTH: 391

```
<212> TYPE: DNA
<213> ORGANISM: Artificial Sequence
<220> FEATURE:
<223> OTHER INFORMATION: Synthetic Promotor

<400> SEQUENCE: 1
gagctcaagc ttgcctcgtc ccgccgggtc acccggccag cgacatggag gcccagaata    60
ccctccttga cagtcttgac gtgcgcagct caggggcatg atgtgactgt cgcccgtaca   120
tttagcccat acatccccat gtataatcat ttgcatccat acattttgat ggccgcacgg   180
cgcgaacgaa aaattacggc tcctcgctgc agacctgcga gcagggaaac gctcccctca   240
cagacgcgtt gaattgtccc cacgccgcgc ccctgtagag aaatataaaa ggttaggatt   300
tgccactgag gttcttcttt cacatacttc cttttaaaat cttgctagga tacagttctc   360
acatcacatc cgaacataaa caaaaactag t                                   391

<210> SEQ ID NO 2
<211> LENGTH: 391
<212> TYPE: DNA
<213> ORGANISM: Artificial Sequence
<220> FEATURE:
<223> OTHER INFORMATION: Synthetic Promotor

<400> SEQUENCE: 2
gagctcaagc ttgcctcgtc ccgccgggtc acccggccag cgacatggag gcccagaata    60
ccctccttga cagtcttgac gtgcgcagct caggggcatg atgtgactgt cgcccgtaca   120
tttagcccat acatccccat gtataatcat ttgcatccat acattttgat ggccgcacgg   180
cgcgaacgaa aaattacggc tcctcgctgc agacctgcga gcagggaaac gctcccctca   240
cagacgcgtt gaattgtccc cacgccgcgc ccctgtagag aaatataaaa catgttagcg   300
ctaccaagtg gttcttcttt cacatacttc cttttaaaat cttgctagga tacagttctc   360
acatcacatc cgaacataaa caaaaactag t                                   391

<210> SEQ ID NO 3
<211> LENGTH: 391
<212> TYPE: DNA
<213> ORGANISM: Artificial Sequence
<220> FEATURE:
<223> OTHER INFORMATION: Synthetic Promotor

<400> SEQUENCE: 3
gagctcaagc ttgcctcgtc ccgccgggtc acccggccag cgacatggag gcccagaata    60
ccctccttga cagtcttgac gtgcgcagct caggggcatg atgtgactgt cgcccgtaca   120
tttagcccat acatccccat gtataatcat ttgcatccat acattttgat ggccgcacgg   180
cgcgaacgaa aaattacggc tcctcgctgc agacctgcga gcagggaaac gctcccctca   240
cagacgcgtt gaattgtccc acatgttagc gctaccaagt aaatataaaa catgttagcg   300
ctaccaagtg gttcttcttt cacatacttc cttttaaaat cttgctagga tacagttctc   360
acatcacatc cgaacataaa caaaaactag t                                   391

<210> SEQ ID NO 4
<211> LENGTH: 391
<212> TYPE: DNA
<213> ORGANISM: Artificial Sequence
<220> FEATURE:
<223> OTHER INFORMATION: Synthetic Promotor

<400> SEQUENCE: 4
```

```
gagctcaagc ttgcctcgtc ccgccgggtc acccggccag cgacatggag gcccagaata    60
ccctccttga cagtcttgac gtgcgcagct caggggcatg atgtgactgt cgcccgtaca   120
tttagcccat acatccccat gtataatcat ttgcatccat acattttgat ggccgcacgg   180
cgcgaacgaa aaattacggc tcctcgctgc agacctgcga gcagggaaac gctcccctca   240
cagacgcgtt gaattgtccc cacgccgcgc cctgtagag aaatataaaa catgttagcg   300
ctaccaagta catgttagcg ctaccaagtc ctttttaaaat cttgctagga tacagttctc   360
acatcacatc cgaacataaa caaaaactag t                                   391
```

```
<210> SEQ ID NO 5
<211> LENGTH: 24
<212> TYPE: DNA
<213> ORGANISM: Artificial Sequence
<220> FEATURE:
<223> OTHER INFORMATION: Nuclear localization signal

<400> SEQUENCE: 5
atgcccaaga agaaaaggaa agtt                                           24

<210> SEQ ID NO 6
<211> LENGTH: 1056
<212> TYPE: DNA
<213> ORGANISM: Saccharomyces cerevisiae

<400> SEQUENCE: 6
```

```
atgaatcaac cagtagaaag acagcgtagg agaactactc aaagtgctac aattcgtgac    60
gtagctgcaa gagcaggtgt ctctcctatg acagtctcac gtgtaatcaa tagagagtcc   120
acagttaaag aggaaactag acagttggtt gaaaaggcaa tagccgacct taactatgct   180
cctaatcctg cagccagatc tttggcaggt agtgcccctt ttagaattgg cttactgtac   240
gataatcctt caactggcta cctttctgaa tttctagttg gtgccttaga tgaatcaagt   300
agaaccggtg ctcaaattgt tatcgagaaa tgtgctgaac cagaattagc cagagctaca   360
cttgctagat tgttgaaaac tggagttgat ggacttatct tacctccacc attatgcgaa   420
tctccagaag ttctggccga gataagagcc gcaggagctg ccgctgtcgc agtggcacct   480
ggtacagctt ctgccgacat ggctactatt agaatcgaca acgaagcagc tgcatttgag   540
ttgacccagc atttgattgg cttgggtcac aaaagattcg gattcattaa gggtcatcca   600
aatcaaaccg tgtctcaaca aaggcttgat gggtttatga ctgctcttaa ggctgcaggg   660
atcccacaag agaatatcag agtggaacaa ggttacttca catatcgttc aggtctagaa   720
gctgcagaga gactactagc agccgaacct aggccaactg ccatcttcgc tgctaacgat   780
gatatggcag ctgcaacagc aggcgtagca catagactag gcttggatgt accaggcgac   840
gtgtctatag tgggatttga tgatacttcc atagctgata catttggcc accattaaca   900 acagttcacc aaccaattgc cgctatggcc agagccgctg ttgatctggt tctagaagag   960
atcagaaggc atagagatgg tggtggcgaa cctagacaat tgatgcatcc acacactctg  1020
atcgttagag actcctcagg ccctgctgga gtctaa                            1056
```

```
<210> SEQ ID NO 7
<211> LENGTH: 1077
<212> TYPE: DNA
<213> ORGANISM: Saccharomyces cerevisiae

<400> SEQUENCE: 7
atgcccaaga agaaaaggaa agttaatcaa ccagtagaaa gacagcgtag gagaactact    60
```

-continued

```
caaagtgcta caattcgtga cgtagctgca agagcaggtg tctctcctat gacagtctca      120
cgtgtaatca atagagagtc cacagttaaa gaggaaacta gacagttggt tgaaaaggca      180
atagccgacc ttaactatgc tcctaatcct gcagccagat ctttggcagg tagtgcccct      240
tttagaattg gcttactgta cgataatcct tcaactggct acctttctga atttctagtt      300
ggtgccttag atgaatcaag tagaaccggt gctcaaattg ttatcgagaa atgtgctgaa      360
ccagaattag ccagagctac acttgctaga ttgttgaaaa ctggagttga tggacttatc      420
ttacctccac cattatgcga atctccagaa gttctggccg agataagagc cgcaggagct      480
gccgctgtcg cagtggcacc tggtacagct tctgccgaca tggctactat tagaatcgac      540
aacgaagcag ctgcatttga gttgacccag catttgattg gcttgggtca caaaagattc      600
ggattcatta agggtcatcc aaatcaaacc gtgtctcaac aaaggcttga tgggtttatg      660
actgctctta aggctgcagg gatcccacaa gagaatatca gagtggaaca aggttacttc      720
acatatcgtt caggtctaga agctgcagag agactactag cagccgaacc taggccaact      780
gccatcttcg ctgctaacga tgatatggca gctgcaacag caggcgtagc acatagacta      840
ggcttggatg taccaggcga cgtgtctata gtgggatttg atgatacttc catagctgat      900
aacatttggc caccattaac aacagttcac caaccaattg ccgctatggc cagagccgct      960
gttgatctgg ttctagaaga gatcagaagg catagagatg gtggtggcga acctagacaa     1020
ttgatgcatc cacacactct gatcgttaga gactcctcag gccctgctgg agtctaa        1077
```

<210> SEQ ID NO 8
<211> LENGTH: 3996
<212> TYPE: DNA
<213> ORGANISM: Saccharomyces cerevisiae

<400> SEQUENCE: 8

```
atgcccaaga agaaaaggaa agttaatcaa ccagtagaaa gacagcgtag gagaactact       60
caaagtgcta caattcgtga cgtagctgca agagcaggtg tctctcctat gacagtctca      120
cgtgtaatca atagagagtc cacagttaaa gaggaaacta gacagttggt tgaaaaggca      180
atagccgacc ttaactatgc tcctaatcct gcagccagat ctttggcagg tagtgcccct      240
tttagaattg gcttactgta cgataatcct tcaactggct acctttctga atttctagtt      300
ggtgccttag atgaatcaag tagaaccggt gctcaaattg ttatcgagaa atgtgctgaa      360
ccagaattag ccagagctac acttgctaga ttgttgaaaa ctggagttga tggacttatc      420
ttacctccac cattatgcga atctccagaa gttctggccg agataagagc cgcaggagct      480
gccgctgtcg cagtggcacc tggtacagct tctgccgaca tggctactat tagaatcgac      540
aacgaagcag ctgcatttga gttgacccag catttgattg gcttgggtca caaaagattc      600
ggattcatta agggtcatcc aaatcaaacc gtgtctcaac aaaggcttga tgggtttatg      660
actgctctta aggctgcagg gatcccacaa gagaatatca gagtggaaca aggttacttc      720
acatatcgtt caggtctaga agctgcagag agactactag cagccgaacc taggccaact      780
gccatcttcg ctgctaacga tgatatggca gctgcaacag caggcgtagc acatagacta      840
ggcttggatg taccaggcga cgtgtctata gtgggatttg atgatacttc catagctgat      900
aacatttggc caccattaac aacagttcac caaccaattg ccgctatggc cagagccgct      960
gttgatctgg ttctagaaga gatcagaagg catagagatg gtggtggcga acctagacaa     1020
ttgatgcatc cacacactct gatcgttaga gactcctcag gccctgctgg agtcggttcc     1080
```

-continued

```
ggaggtggag gttctatgaa tccgggcggt gaacaaacaa taatggaaca acccgctcaa    1140
cagcaacaac aacagcaaca acaacagcag caacagcaac agcaggcagc agttcctcag    1200
cagccactcg acccattaac acaatcaact gcggaaactt ggctctccat tgcttctttg    1260
gcagaaaccc ttggtgatgg cgacagggcc gcaatggcat atgacgccac tttacagttc    1320
aatccctcat ctgcaaaggc tttaacatct ttggctcact tgtaccgttc cagagacatg    1380
ttccaaagag ctgcagaatt atatgaaaga gcacttttgg taaatcccga actatcagat    1440
gtgtgggcta cttaggtca ttgttatctg atgctggatg atctgcaaag agcttacaat    1500
gcctatcaac aggctctcta ccacctcagt aatcccaacg taccgaaatt atggcatgga    1560
atcggcattc tttatgacag atatggttcg ctcgactatg ccgaagaagc ttttgccaaa    1620
gttttggaat tggaccctca ttttgaaaag gcaaacgaaa tttacttcag actaggtatt    1680
atttataaac atcagggtaa atggtctcaa gctttggaat gcttcagata cattctccct    1740
caacctcctg ctcccttgca ggagtgggac atatggtttc agttgggtag tgttttggag    1800
agtatgggag agtggcaagg tgcgaaggaa gcctacgagc atgtcttggc tcaaaatcaa    1860
catcatgcca aagtattaca acaattaggt tgtctttacg gtatgagtaa cgtacaattt    1920
tatgaccctc aaaaggcatt ggattatctt ctaaagtcgt tagaagcaga tccctccgat    1980
gccactacat ggtaccatct cggtagagtg catatgatta gaacagatta tactgccgca    2040
tatgatgctt tccaacaagc tgttaataga gattcaagaa accctatctt ttggtgctca    2100
atcggtgttt tatattacca aatttctcaa tacagagacg ccttagacgc gtacacaaga    2160
gccataagat taaatcctta tattagtgaa gtttggtacg atctaggtac tctttacgaa    2220
acttgtaaca accaattatc tgacgccctt gatgcgtata agcaagctgc aagactggac    2280
gtaaataatg ttcacataag agaaagatta gaagctttaa caaagcagtt agaaaaccca    2340
ggcaatataa acaaatcgaa cggtgcgcca acgaatgcct ctcctgcccc acctcctgtg    2400
attttacaac ctaccttaca acctaatgat caaggaaatc ctttgaacac tagaatttca    2460
gcccaatctg ccaatgctac tgcttcaatg gtacaacaac agcatcctgc tcaacaaacg    2520
cctattaact cttctgcaac aatgtacagt aatggagctt cccctcaatt acaagctcaa    2580
gctcaagctc aagctcaagc acaagctcaa gcacaagcac aagctcaagc acaagcacaa    2640
gcacaagcgc aagcacaagc acaagcacag gcgcaagcac aggcacaagc acaagcacaa    2700
gcacatgcac aagcgcaagc acaagcacaa gcacaggcac aagcacaagc acaggcgcag    2760
gcacaacaac aacaacaaca acagcaacaa caacaacaac aacaacaaca acaacaacaa    2820
caacaacaac aacaacaaca acaacagcag cagcaattac agcccctacc aagacaacag    2880
ctgcagcaaa agggagtttc tgtgcaaatg ttaaatcctc aacaagggca accatatatc    2940
acacagccaa cagtcataca agctcaccaa ctgcaaccat tttctacaca agctatggaa    3000
catccgcaaa gctctcaact gccacctcaa cagcaacaac tacaatctgt tcaacatcca    3060
caacaacttc aaggccagcc tcaagcccaa gctccccaac ctttaatcca gcataacgtg    3120
gaacagaacg tttttacctca aaagagatac atggaaggtg caatccacac tttagtagat    3180
gccgccgtat ccagtagcac ccacacagag aataacacaa agtctcctcg tcaaccaacc    3240
catgccattc caacgcaagc tcccgcaaca ggaataacga acgctgaacc acaggtaaag    3300
aagcaaaagt tgaactctcc aaattcaaac atcaacaaat tagtaaatac tgctacttcc    3360
attgaagaaa atgcaaaatc tgaggtgagc aaccaatcgc cagcagtagt ggagtctaat    3420
accaataata cttcacaaga agaaaaacct gtaaaagcaa actcaatacc ttcagtaatt    3480
```

```
ggcgcacagg aacctccaca ggaagctagt cctgctgaag aagctaccaa agcagcttct    3540
gtttctcctt ctacaaaacc gcttaatacg gaaccagagt catctagtgt ccaaccaact    3600
gtatcatcag aaagttcaac aacaaaagca aatgaccaaa gcactgctga gaccatagaa    3660 cttttctactg ctactgttcc tgcagaagca agccctgtag aagacgaagt aagacagcat    3720
tctaaagagg aaaacggcac aactgaagca tctgcacctt ctactgaaga ggcggagcca    3780
gcagcttcca gagatgctga aaaacaacaa gatgaaaccg ctgctacaac gataactgta    3840
atcaaaccta ctttggaaac aatggaaaca gtgaaagagg aggccaaaat gcgtgaggaa    3900
gagcaaacat ctcaagaaaa atccccacag gagaacacac ttccaagaga aaatgtagta    3960
aggcaagtgg aagaagatga aaactacgac gactaa                              3996

<210> SEQ ID NO 9
<211> LENGTH: 395
<212> TYPE: DNA
<213> ORGANISM: Artificial Sequence
<220> FEATURE:
<223> OTHER INFORMATION: Synthetic Promoter

<400> SEQUENCE: 9
gagctcaagc ttgcctcgtc ccgccgggtc acccggccag cgacatggag gcccagaata     60
ccctccttga cagtcttgac gtgcgcagct caggggcatg atgtgactgt cgcccgtaca    120
tttagcccat acatcacatg ttagcgctac caagttgcat ccatacattt tgatggccgc    180
acggcgcgaa cgaaaaatta cggctcctcg ctgcagacct gcgagcaggg aaacgctccc    240
ctcacagacg cgttgaattg tccccacgcc gcgcccctgt agagaaatat aaaaggttag    300
gatttgccac tgaggttctt ctttcacata cttccttta aaatcttgct aggatacagt    360
tctcacatca catccgaaca taaacaaaaa ctagt                               395

<210> SEQ ID NO 10
<211> LENGTH: 395
<212> TYPE: DNA
<213> ORGANISM: Artificial Sequence
<220> FEATURE:
<223> OTHER INFORMATION: Synthetic Promoter

<400> SEQUENCE: 10
gagctcaagc ttgcctcgtc ccgccgggtc acccggccag cgacatggag gcccagaata     60
ccctccttga cagtcttgac gtgcgcagct caggggcatg atgtgactgt cgcccgtaca    120
tttagcccat acatcacatg ttagcgctac caagttgcat ccatacattt tacatgttag    180
cgctaccaag tgaaaaatta cggctcctcg ctgcagacct gcgagcaggg aaacgctccc    240
ctcacagacg cgttgaattg tccccacgcc gcgcccctgt agagaaatat aaaaggttag    300
gatttgccac tgaggttctt ctttcacata cttccttta aaatcttgct aggatacagt    360
tctcacatca catccgaaca taaacaaaaa ctagt                               395

<210> SEQ ID NO 11
<211> LENGTH: 395
<212> TYPE: DNA
<213> ORGANISM: Artificial Sequence
<220> FEATURE:
<223> OTHER INFORMATION: Synthetic Promoter

<400> SEQUENCE: 11
gagctcaagc ttgcctcgtc ccgccgggtc acccggccag cgacatggag gcccagaata     60
```

```
                                        -continued ccctccttga cagtcttgac gtgcgcagct caggggcatg atgtgactgt cgcccgtaca     120
tttagcccat acatcacatg ttagcgctac caagttgcat ccatacattt tacatgttag     180
cgctaccaag tgaaaaatta cggctcctcg ctgcagacct gcgagcaggg aaacgctccc     240
ctcacagacg cgttgaattg tccccacgcc gcgcccctgt agagaaatat aaaacatgtt     300
agcgctacca agtacatgtt agcgctacca agtccttta aaatcttgct aggatacagt      360
tctcacatca catccgaaca taaacaaaaa ctagt                                 395

<210> SEQ ID NO 12
<211> LENGTH: 20
<212> TYPE: DNA
<213> ORGANISM: Artificial Sequence
<220> FEATURE:
<223> OTHER INFORMATION: Synthetic Promoter

<400> SEQUENCE: 12
acatgttagc gctaccaagt                                                   20
```